United States Patent
Clark et al.

(10) Patent No.: US 6,428,960 B1
(45) Date of Patent: Aug. 6, 2002

(54) SELECTION METHOD FOR PRODUCING RECOMBINANT BACULOVIRUS

(75) Inventors: Robin Clark, Benecia; Joanna Albala, Stockton; Ian McConnell, Danville, all of CA (US); Ken Franke, Gaithersburg, MD (US)

(73) Assignee: Onyx Pharmaceuticals, Inc., Richmond, CA (US)

( * ) Notice: Subject to any disclaimer, the term of this patent is extended or adjusted under 35 U.S.C. 154(b) by 0 days.

(21) Appl. No.: 09/702,181

(22) Filed: Oct. 30, 2000

Related U.S. Application Data

(63) Continuation-in-part of application No. 09/262,941, filed on Mar. 4, 1999, now Pat. No. 6,225,060.
(60) Provisional application No. 60/076,773, filed on Mar. 4, 1998.

(51) Int. Cl.[7] .................. C12Q 1/68; C12P 21/04; C07H 21/04
(52) U.S. Cl. .................. 435/6; 435/69.7; 435/70.1; 536/23.72
(58) Field of Search .................. 435/6, 69.7, 70.1; 536/23.72

(56) References Cited

PUBLICATIONS

References cited in the parent application, 09/262,941, have been considered.*

* cited by examiner

*Primary Examiner*—Hankyel T. Park
(74) *Attorney, Agent, or Firm*—Gregory Giotta

(57) ABSTRACT

The present invention provides a novel method for producing recombinant baculoviruses expressing genes of interest by inserting a selectable marker gene, specifically the puromycin resistance (pac) gene, adjacent to the gene of interest into the baculovirus genome, and selecting for viruses that express the selectable marker. Selection of the recombinant virus in the presence of a selection condition, such as puromycin-containing cell culture media, simplifies virus production by eliminating the need for cloning, and testing the virus for gene expression. Such expression systems are readily adapted to an automated method for expression foreign genetic material in a high throughput manner.

15 Claims, 5 Drawing Sheets

SELECTION METHOD FOR PRODUCING RECOMBINANT BACULOVIRUS

This application is a continuation-in-part of U.S. patent application Ser. No. 09/262,941, now U.S. Pat. No. 6,225,060, filed on Mar. 4, 1999, which claims priority from U.S. Provisional Application No. 60/076,773, filed on Mar. 4, 1998.

FIELD OF THE INVENTION

The present invention relates generally to the field of molecular biology and genetics. Specifically, the present invention relates to a method for producing recombinant baculovirus expressing a gene of interest by selecting for puromycin resistance that is conferred by that baculovirus.

BACKGROUND OF THE INVENTION

Baculoviridae comprise a family of viruses that infect insect cells, and can be genetically modified to serve as transfer and expression vectors for a highly productive recombinant protein expression system in the eukaryotic host. (Summers and Smith, *Tex. Agric. Exp. Stn. Bull.* B1555: 1–55 (1987); Davies, Bio/technology 12:47–50 (1994)). Exemplary baculoviruses include but are not limited to *Autographa californica*, Trichoplusia ni, Rachiplusia ou, *Galleria mellonella* and *Bombyx mori*. Of these, *Autographa californica* is probably the most fully characterized and widely used. The polyhedrin gene of baculoviruses is expressed at very high levels during the natural viral life cycle, but is dispensable in cell culture. This allows it to be replaced by almost any heterologous nucleotide sequence of interest. Any heterologous nucleotide of interest inserted so as to replace the polyhedrin gene may itself be controlled by the polyhedrin promoter, and thus expressed to similarly high levels.

Advantages of the baculovirus expression system include: (1) avirulence of baculoviruses in humans, (2) facility of protein expression in milligram quantities, and (3) ability of insect cells to grow at ambient temperature without the need for carbon dioxide (Kidd and Emery, 1993). Although both prokaryotic and eukaryotic cells have been used to express foreign genetic material, prokaryotic cells such as *Escherichia coli* are suitable for expressing foreign genetic material only if the gene product does not require post-translational modification such as glycosylation, phosphorlyation or signal peptide cleavage. Prokaryotic cells do not contain the machinery needed for such post-translational modification. Eukaryotic cells, such as insect cells which baculoviruses infect accomplish most eukaryotic post-translational modifications, including phosphorylation, N- and 0-linked glycosylation, acylation, disulphide cross-linking, oligomeric assembly and subcellular targeting which may be critical for the biological integrity of recombinant proteins (Davies, 1994). In contrast to the more commonly used bacterial expression systems, recombinant baculoviral expression generally produces soluble proteins without the need for induction or specific temperature conditions.

Manipulation of baculovirus genomes at the molecular level is challenging, as they comprise some 130 kb of DNA too large to be amenable to conventional plasmid cloning techniques. The traditional solution to this problem has been to introduce foreign genes by homologous recombination, as a cassette also comprising suitable promoter and termination sequences. This is accomplished by flanking the cassette, in a plasmid vector, by the viral DNA sequences which flank the point at which it is to be inserted. The efficiency of this process is usually less than 1%.

In the past, plaque purification has been used to proceed from this point to a clonal vector. Some traditional procedures are described by Smith et al., U.S. Pat. No. 4,745,051, Smith et al, U.S. Pat. No. 4,879,236, Summers et al., U.S. Pat. No. 5, 169,784, Guarino et al., U.S. Pat. No. 5,077,214, Kang, U.S. Pat. No. 5,194,376, Matsuura et al, U.S. Pat. No. 5,229,293 and Murphy et al., U.S. Pat. No. 5,516,657, the disclosures of which are herein incorporated by reference. Recently, however, several different techniques have been developed to increase the frequency of recombination into the baculovirus genome. The most successful of these are described, infra.

The baculovirus genome has been reconstituted as a replicon which will propagate in the yeast *Saccharomyces cerevisia*. This was achieved by inserting a yeast Autonomously Replicating Sequence (ARS) into the polyhedrin locus of the baculovirus genome, along with a CEN (centromeric) sequence, which ensures stable low copy number segregation of the genome by acting as a mitotic centromere, and the URA3 selectable marker, to permit growth in a uracil-free medium. Thus the recombination of a polyhedrin promoter-driven foreign gene may be undertaken in yeast, and the resulting baculovirus genome extracted from the yeast cells and transfected directly into insect cells as a clonal virus. Advantages of this method include near 100% efficiency and the ability to manipulate in a foreign host genes whose products might be toxic to insect cells. However, a large number of manipulations are required making this procedure cumbersome and complicated.

The baculovirus genome has also been reconstituted as a replicon which may propagate in *Escherichia coli*. In a similar approach to that used in yeast, Luckow et al., *J. Virology*, 67: 4566–4579, initially demonstrated that the baculovirus genome may be modified to replicate as a large plasmid in *Escherichia coli*, termed a 'bacmid'. This may be performed by recombining a mini-F replicon into the polyhedrin locus, conferring autonomous replication and stable, low-copy number segregation of the genome, and the kanr selectable marker. The target site for the Tn7 bacterial transposon may also be introduced, as an in-frame insertion within the lacZa sequence from a pUC-based plasmid. This bacmid may therefore intra-allelically complement the defective β-galactosidase lacZDM15 of *Escherichia coli* hosts such as DH 1 OB. However, *Escherichia coli* DH1OB harboring a bacmid with a foreign gene inserted at this Tn7 site would remain lacZa−, enabling visual selection of colonies containing recombinant bacmids. The overall strategy of such a procedure is to accomplish the recombination and selection steps in the heterologous host, here *Escherichia coli*, and only then to transfer the finished product to insect cells. This strategy has similar advantages to the yeast system but also involves many steps.

Rather than reconstitute the baculovirus replicon in a heterologous host considered preferable for selection of recombinant species, an in vitro recombination reaction to transfer genes from transfer vectors to the polyhedrin locus of the virus has been developed. Exploiting the Cre recombinase of bacteriophage Pi and its substrate lovp, the gene transfer in this system is achieved by a single enzymatic crossover reaction. Both the target baculovirus genome (vaclox) and the transfer vector are engineered to contain lox sites. These 34 nucleotide sequences direct the Cre enzyme to convert the two substrate DNA molecules into topologically unlinked, recombinant products. The reaction proceeds stoichiometrically, with an efficiency of around 70%. This approach has the great advantage of simplicity, however, the maximum efficiency is only about 70%.

In 1990, Kitts et al., *Nucl. Acids Res.* 18:5667–5672 (1990) derivatised wild-type baculovirus DNA, which exists as a covalently closed circular double-stranded molecule, by introducing a unique restriction site (Bsu361) at the polyhedrin locus. Linearising the baculovirus genome using this restriction site reduces the infectivity of the viral DNA on transfection into insect cells, however, cotransfection with a transfer vector driving recombination into the polyhedrin locus produces a three fold higher proportion of recombinant viruses.

In this strategy, the baculovirus containing the Bsu361 site was designated ACRP-SC (for single cut), and the two double crossover events transferring the foreign gene to be expressed, along with its own copy of the polyhedrin promoter and terminator sequences, are also present. About 10 to 25% of the progeny viruses from such a cotransfection are recombinant, but it should be noted that this is due to the reduced background of wild type viruses rather than an increase in the absolute number of recombinants.

A subsequent development of this system effectively combines it with both a visual (lacZ-based) and a replication-based selection strategy. Kitts et al., *Biotechniques* 14:810–817 (1993). Recombination occurs between a conventional transfer vector and a derivative of the wild type genome, containing lacZ at the polyhedrin locus and two further Bsu361 sites in the polyhedrin flanking sequences (designated BacPAK6). Bsu361 digestion of this baculovirus DNA not only linearizes the molecule, but also removes two genomic fragments, thus disrupting the open reading frame ORF-1629. This gene is essential for baculovirus replication, so, with the two Bsu361 fragments removed from the genome, competent viruses will only be reconstituted by recombination with the transfer vector, whereby an intact ORF-1629 will be restored to the genome. Furthermore, recombinant viruses will form white plaques on a background of blue plaques from BacPAK6 DNA.

This strategy yields recombinant viruses at a frequency of 85–99%. The majority of the background may be attributed to contamination with undigested BacPAK6 DNA, which will be substantially more infectious than linear forms of the genome. Viruses which offer the prospect of utility for future work, which are likely to be a small minority of the total number of viruses generated, may then be purified by conventional technology (plaque assays). Therefore this method offers a good combination of simplicity and efficiency, and will be our technique of choice for converting arrayed cDNAs into expression vectors.

One particular problem associated with baculovirus expression systems is that they may produce apoptosis or cell lysis of infected cells. A baculovirus apoptosis resistance gene (p35 gene) has been identified that confers increased viral yield in certain cell lines. Recombinant baculoviruses bearing this gene can selectively amplified (up to $10^6$ fold) in appropriate hosts.

Despite the useful combination of high yields and authenticity of processing associated with baculovirus expression systems, purification of the desired product from baculovirus infected cells is no easier than from any other eukaryotic system. Many expression vectors have been developed enabling synthesis of the antigen of interest as a fusion with a polypeptide facilitating purification. For instance, protein A fusion proteins may be affinity purified on IgG, polyarginine fusion proteins may be purified by cation exchange, polyhistidine fusions may be purified by virtue of their chelation of zinc ions, β-galactosidase fusions, and other fusions to specifically immunogenic partners, may be purified by immunoaffinity, and β-galactosidase, maltose binding protein and glutathione-S-transferase (GST) fusion proteins may be purified by substrate affinity. Other epitope tags such as those recognized by the EE or Glu-Glu antipeptide antibody may also be used. This antibody was raised against a peptide that comprises the major tyrosine phosphorylation site of polyoma middle t antigen. This tag has been used extensively in many recombinant applications. Some investigators report that over 90% of attempts to purify EE-tagged proteins have been successful, most of these to over 50% purity with no other chromatographic steps (Jim Litts and Robin Clark unpublished data).

The epitope for this tag has been fully characterized and optimized by NEmotope peptide scan analysis (Mario Geysen, John Wang and Robin Clark unpublished data). The antibody has a moderate affinity for the EE tag (Kd-$2\times10^{-7}$) hich allows rapid elution of tagged proteins by free peptide under non-denaturing conditions while retaining efficient binding of proteins in crude lysates. While sually placed at the N-terminus, the EE tag is also recognized when placed at the C-terminus or at internal portions of the protein. An antibody to the tag is also useful or immunoprecipitates, inumunoflourescence and western blots. Moreover, the ntibody is produced at high levels by the EE hybridoma. Some have reported that 10 preps routinely yield 3–5 g of purified antibody. The EE tag has the additional advantage of containing a strong tyrosine phosphorylation substrate for protein kinases such as src. Such a tag may be directly labeled with radioactive phosphate or detected with an anti-phosphotyrosine antibody.

Several resistance genes have been used as selectable markers in a variety of expression vectors to enhance selection of recombinants. (Old and Primrose, Principles of Gene Manipulation, Oxford: Blackwell Scientific Publications, 1991, pp. 259–262; Karreman, *Gene* 218 (1–2): 57–61 (1998)). In 1993, a novel puromycin-resistancedeterminant (pur8) was isolated from the puromycin gene cluster that encodes the puromycin biosynthetic pathway from *Streptomyces alboniger* and expressed in *Streptomyces lividans*. The gene induced antibiotic resistance that was highly specific for puromycin. The polypeptide product referred to as Pur8 consists of 14 possble transmembrane—spanning segments, and shows significant similarities to other known or putative transmembrane proteins, including several which confer drug resistance in a variety of antibiotic—producing Streptomyces, Gram-positive and Gram-negative bacteria, and some solute transporters of prokaryotic and eukaryotic origin. (Tercero, et al., *Eur. J Biochem.* 218(3): 963–971 (1993)) The novel puromycin acetyltransferase, has been used as a selectable marker gene, and can be expressed under the control of the *Drosophila melanogaster* hsp 70 promotor or AcMNPV ie-1 promoter which is active in *Spodopterafrugiperda* cells in the absence of virus infection. Expression vectors have been constructed which co-express two genes from separate promoters, the pac gene which confers resistance to puromycin and a selectable baculovirus gene which inhibits apoptosis. (McLachlin and Miller, In *Vitro Cell Dev. Biol. Anim.* 33(7):575–579 (1997)) The puromycin resistance gene (PAC) has also been used as a positive selectable marker in mammalian cells, (Karreman, *Gene* 218(1–2): 57–61 (1998)) and in single-transcript vectors, where it is expressed from the internal ribosomal entry site of encephalomyocarditis virus (Levenson, et al., *Hum. Gene Ther.*, 9(8): 1233–1236 (1998)).

This invention is a method for producing recombinant baculoviruses, without utilizing cloning steps, expressing genes of interest by inserting a selectable marker gene, specifically the puromycin resistance (pac) gene, adjacent to the gene of interest into the baculovirus genome, and selecting for viruses that express the selectable marker. The majority of the selected viruses should express the gene of interest. Selection of the recombinant virus in the presence of a selection condition, such as puromycin-containing cell culture media, simplifies virus production by eliminating the need for cloning and testing the virus for gene expression.

SUMMARY OF THE INVENTION

In one aspect, the present invention features a novel baculovirus expression system especially adept at expressing heterologous genetic material in a host. Generally, such systems comprise one or more selectable marker genes, a promoter such as a polyhedrin promoter of a polyhedrin structural gene or a fragment thereof, a transcription terrnination sequence such as a transcription termination sequence of a polyhedrin structural gene or fragment thereof, a cloning site operable to accept foreign genetic material, optionally a tag and optionally one or more restriction sites. Exemplary selectable marker genes include the puromycin resistance (pac) gene, and exemplary tags include the EE tag sequence. In preferred embodiments, the ORF-1629 gene is also present in the baculovirus expression system and is used as a second selectable marker gene. The invention features a method for producing recombinant baculovirus in which a DNA fragment containing foreign genetic material is used to combine preferably two selectable marker genes into a single DNA fragment, which when co-transfected with Baculovirus DNAs into insect host cells, yields a recombinant baculovirus which can be isolated by selection of selectable marker genes. Therefore, the present invention can be used to produce recombinant baculovirus without utilizing cloning steps, and thereby is useful for automated high throughput expression systems.

In a second aspect, the present invention features a method for producing a recombinant baculovirus expression system comprising the steps of (a) providing a baculovirus transfer vector comprising a puromycin resistance (pac) gene, a promoter such as a polyhedrin promoter of a polyhedrin structural gene or a fragment thereof, a transcription termination sequence such as a transcription termination sequence of a polyhedrin structural gene or fragment thereof, a cloning site operable to accept foreign genetic material, optionally a tag and optionally one or more restriction sites, and (b) ligating foreign genetic material into the baculovirus transfer vector at the cloning site such that the foreign genetic material is under the control of the promoter.

In a third aspect, the present invention features a method for expressing foreign genetic material comprising the steps of: (a) providing a baculovirus transfer vector comprising a puromycin resistance (pac) gene, a promoter such as a polyhedrin promoter of a polyhedrin structural gene or a fragment thereof, a transcription termination sequence such as a transcription termination sequence of a polyhedrin structural gene or fragment thereof, a cloning site operable to accept foreign genetic material, optionally a tag and optionally one or more restriction sites, (b) ligating foreign genetic material into the baculovirus transfer vector at the cloning site such that the foreign genetic material is under the control of the promoter, and (c) transfectipg the baculovirus transfer vector comprising the foreign genetic material into a host cell. In preferred embodiments, the present invention is adapted to automation and thereby is useful for high throughput expression.

In a fourth aspect, the present invention features a method for determining the function of foreign genetic material comprising the steps of: (a) providing a baculovirus transfer vector comprising a puromycin resistance (pac) gene, a promoter such as a polyhedrin promoter of a polyhedrin structural gene or a fragment thereof, a transcription termination sequence such as a transcription termination sequence of a polyhedrin structural gene or fragment thereof, a cloning site operable to accept foreign genetic material, optionally a tag and optionally one or more restriction sites, (b) ligating foreign genetic material into the baculovirus transfer vector at the cloning site such that the foreign genetic material is under the control of the promoter, (c) transfecting the baculovirus transfer vector comprising the foreign genetic material into a host cell, and (d) observing the biological results produced thereby. In preferred embodiments, the present invention is adapted to automation and thereby is useful for high throughput analysis.

In a fifth aspect, the present invention features genes and fragments thereof, nucleotide sequences, and gene products obtained by way of the method of the present invention. The present invention features expressing selected nucleotide sequences in a host organism. Those of skill in the art will readily appreciate that the gene products of such nucleotide sequences may be isolated and purified using techniques known to those skilled in the art. Such isolation and purification techniques may be optimized according to some of the methods described herein. Such gene products may exhibit biological activity as pharmaceuticals and other similar functions.

BRIEF DESCRIPTION OF THE FIGURES

RGus virus was serially diluted in 10-fold increments. After addition of virus dilutions, the plate was incubated for several days, and then X-glucuronide stock was added to each well. X-glucuronide is a histochemical substrate for β-glucuronidase, yielding a blue substrate upon hydrolysis. Blue color development was visible in many wells within minutes after addition of the substrate, and color development continued to occur in high dilution wells over 24 hours as rGus production increased in infections resulting from low MOI's FIG. 4 demonstrates the results obtained when Millipore MAIP N45 high protein binding plates containing Immobilon-P filtration membranes were treated with either Glu-tagged or GST-tagged proteins and assayed for binding using a monoclonal anti-Glu Glu antibody and an alkaline phosphatase conjugated goat anti-mouse IgG secondary antibody. Alkaline phosphatase was detected using Sigma-Fast BCIP/NBT tablets. These data demonstrate that purified Rho-EE, E2 F-EE and Mutl-EE were detected at concentrations ranging from 0.1 to 2.0 $\mu$g/well

DETAILED DESCRIPTION OF THE INVENTION

Figure 1:
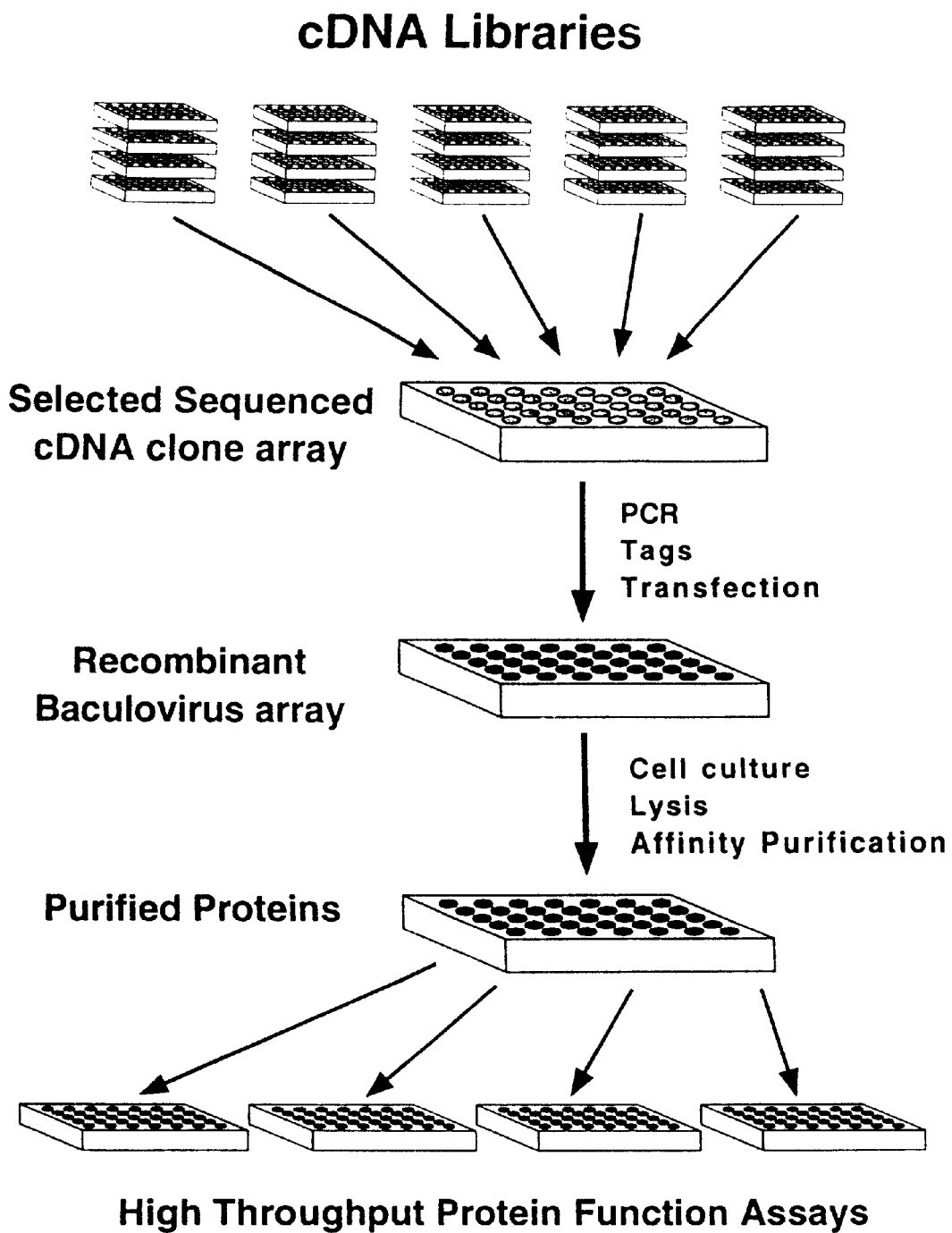
FIG. 1 demonstrates a general schemata for a high throughput protein function assay which may be performed according to the methods of the present invention. Selected cDNA clones may be amplified, optionally tagged and transfected into recombinant baculovirus transfer vector which have been linearized in an arrayed configuration. The recombinant baculovirus expression systems may in turn be transfected into suitable host cells such as insect cells. The product of the foreign genetic material may be purified by any suitable purification protocol such as affinity means. Optionally, the purified proteins may then be further analyzed in order to determine the biological activity and/or function thereof.

In one aspect, the present invention features novel baculovirus expression systems especially adept at expressing heterologous genetic material in an insect host. Generally, such systems comprise one or more selectable marker genes, a promoter such as a polyhedrin promoter of a polyhedrin structural gene or a fragment thereof, a transcription termination sequence such as a transcription termination sequence of a polyhedrin structural gene or fragment thereof, a cloning site operable to accept foreign genetic material, optionally a tag and optionally one or more restriction sites. Exemplary selectable marker genes include the ORF-1629 gene and the puromycin resistance (pac) which may be located upstream from a polyhedrin promoter in many embodiments, and which may be located downstream from the transcription termination sequence in many embodiments. Exemplary tags include the EE tag sequence.

In some embodiments, the present invention features recombinant baculoviruses that are generated by transfecting insect cells with ligated fragments containing transfer vector elements, selectable markers and cDNA as opposed to cloned transfer vector plasmids as taught by the prior art. Therefore, the baculovirus expression systems of the present invention greatly simplify the methods of the prior art by eliminating the plasmid cloning steps and by allowing the expression of cDNA which cannot be cloned in bacteria. In this embodiment, selectable markers residing on separate fragments may be joined to fragments containing a cDNA coding sequence. This provides for the selection of recombinant baculoviruses which contain the desired cDNA. Any method suitable for joining DNA fragments may be applied for this purpose.

The recombinant baculovirus expression systems of the present invention comprise in the most preferred embodiments a puromycin resistance (pac) gene encoding the puromycin resistance protein, a polyhedrin promoter, foreign genetic material under the control of the polyhedrin promoter and cloned into the baculovirus at cloning sites, a tag sequence such as the EE tag either upstream or downstream from the cloning site and a ORF-1629 gene which is believed to be important for baculovirus replication and/or infectivity. It is further contemplated that convenient restriction sites will be found both upstream and downstream from all of these elements though they need not be adjacent to any one particular element. Such convenient restriction sites include but are not limited to a XhoI site and a PvuII site.

In a second aspect, the present invention features a method for producing a recombinant baculovirus expression system comprising the steps of (a) providing a baculovirus transfer vector comprising one or more selectable markers, a promoter such as a polyhedrin promoter of a polyhedrin structural gene or a fragment thereof, a transcription termination sequence such as a transcription termination sequence of a polyhedrin structural gene or fragment thereof, a cloning site operable to accept foreign genetic material, optionally a tag and optionally one or more restriction sites, and (b) ligating foreign genetic material into the baculovirus transfer vector at the cloning site such that the foreign genetic material is under the control of the promoter. In the preferred embodiment, generation of the selected virus is accomplished by constructing a piece of linear or circular DNA containing both the selectable marker (pac) gene, the gene of interest and preferably one or more additional selectable markers which are co-expressed during viral infections. The piece of DNA is also constructed so as to contain recombinigenic sites that are located outside of the assembly containing the gene of interest and selectable markers. The recombinegenic sites direct the insertion of the piece of DNA into the viral DNA using any type of in vitro or in vivo recombination mechanism.

In some embodiments such a recombinant baculovirus expression system may be produced in an automated or high throughput fashion. It is specifically contemplated that an operable portion of a baculovirus comprising a puromycin resistance (pac) gene, a promoter such as a polyhedrin promoter of a polyhedrin structural gene or a fragment thereof, a transcription termination sequence such as a transcription termination sequence of a polyhedrin structural gene or fragment thereof, a cloning site operable to accept foreign genetic material, optionally a tag may be removed from the baculovirus genome using restriction enzymes.

In such embodiments of the present invention wherein recombinant baculovirus expression systems are produced using automation, high yields may be produced in a relatively short period of time. Using such technology, such genetic material as cDNA may be arrayed for insertion at a cloning site so that recombinant baculoviruses containing many differing inserts may be provided.

In a third aspect, the present invention features a method for expressing foreign genetic material comprising the steps of: (a) providing a baculovirus transfer vector comprising a puromycin resistance (pac) gene, a promoter such as a polyhedrin promoter of a polyhedrin structural gene or a fragment thereof, a transcription termination sequence such as a transcription termination sequence of a polyhedrin structural gene or fragment thereof, a cloning site operable to accept foreign genetic material, optionally a tag and optionally one or more restriction sites, (b) ligating foreign genetic material into the baculovirus transfer vector at the cloning site such that the foreign genetic material is under the control of the promoter, and (c) transfecting the baculovirus comprising the foreign genetic material into a host cell.

It is generally contemplated that in preferred embodiments the host cell is an insect cell. Sf9 has been specifically demonstrated as a particularly promising animal cell host for the recombinant production of proteins according to some embodiments of the present method.

It is specifically contemplated that the cloning of foreign genetic material and isolation and purification of the products obtained from the expression thereof may be automated. The technologies allowing parallel processing of samples are a combination of organizational formats, particularly the widespread use of 96 and 384 well microtiter plates and the increasing use of sample handling robots designed to rapidly and systematically work with such organizational formats. For instance, the 96 well round microtiter plate was initially developed specifically for use in the field of immunology, but the 384 well was developed by Lawrence Livermore National Laboratory for use in genome research. Moreover, early robots have been designed for use with the 384 plates to facilitate genomic research. Copeland et al., *Nature* 369:421–422 (1994).

Concomitant with the formatting and automation developments, cloned samples of genomic DNA and complementary DNA, hereinafter referred to as cDNA, have increasingly been provided in such formatted arrays. For instance, cosmid and phage libraries containing inserts primarily from single human chromosomes isolated by flow-sorting were provided by Lawrence Livermore National Laboratories and Los Alamos National Laboratory as part of the Department of Energy's National Gene Library Project. Recently, cDNA clones have become available in large numbers through the I.M.A.G.E. (Integrated Molecular Analysis of Genomes and their Expression) Consortium at Lawrence Livermore National Laboratories. Lennon et al., *Genomics* 33:151–152 (1996).

The I.M.A.G.E. Consortium promotes the use of shared and arrayed cDNA libraries. In partnership with Washington University (Hillier et aL, *Genome Research* 6:829–845 (1996)), sequences from these publicly available clones are deposited without restriction or delay in the public sequence databases, a database containing short sequence tags or Expressed Sequence Tags (dbEST). Over 500,000 human cDNA clones have been arrayed, and over 500,000 sequences are available in dbEST. Sequence clustering algorithms indicate that the majority of the 80,000 or so human genes are now likely to be represented by clones in this collection. Hillier, supra; Aaronson et al., *Genome Research* 6:829–845 (1996).

The majority of clones available in the I.M.A.G.E. cDNA collection are from dT-primed mRNA, and the average length is between 1–2 kb. Therefore, the collection more fully represents the 3'1–2 kb portion of many mRNAs but provides less coverage of 5' and coding sequences. Of the 4,200 human mRNAs collated in the human non-redundant mRNA set (NCBI), approximately 25% are fully represented by an I.M.A.G.E. clone, 50% have a partial representative, and less than 25% lack any representative clone. Based upon resequencing of clones, the estimated overall error rate presently is about 9%. Thus, about 91% of the time, a clone thought to reside in a particular microtiter plate location is indeed the one grown up from that plate well.

It is specifically intended that these cDNA clones be used to provide the foreign genetic material according to the present invention. Moreover, it is fully contemplated that additional libraries from other biological sources and arrayed in differing manners may be suitably adapted to the present method without undue experimentation.

Despite the high yields and authenticity of processing associated with recombinant baculovirus expression systems, purification of the desired product from baculovirus infected cells is no easier than from any other eukaryotic system. Many expression vectors have been developed enabling synthesis of the antigen of interest as a fusion with a polypeptide facilitating purification. For instance, protein A fusion proteins may be affinity purified on IgG, polyarginine fusion proteins may be purified by cation exchange, polyhistidine fusions may be purified by virtue of their chelation of zinc ions, β-galactosidase fusions, and other fusions to specifically immunogenic partners, may be purified by immunoaffinity, and β-galactosidase, maltose binding protein and glutathione-S-transferase (GST) fusion proteins may be purified by substrate affinity. Other epitope tags such as those recognized by the EE or Glu-Glu antipeptide antibody may also be used. This antibody was raised against a peptide that comprises the major tyrosine phosphorylation site of polyoma middle t antigen. This tag has been used extensively in many recombinant applications. Some investigators report that over 90% of attempts to purify EE-tagged proteins have been successful, most of these to over 50% purity with no other chromatographic steps (Jim Litts and Robin Clark unpublished data).

The epitope for this tag has been fully characterized and optimized by NEmotope peptide scan analysis (Mario Geysen, John Wang and Robin Clark unpublished data). The antibody has a moderate affinity for the tag (Kd $2\times10^{-7}$) which allows rapid elution of tagged proteins by free peptide under non-denaturing conditions while retaining efficient binding of proteins in crude lysates. While usually placed at the N-terminus, the tag is also recognized when placed at the C-terminus or at internal portions of the protein. The antibody is also useful for immunoprecipitates, immunoflourescence and western blots. Moreover, this antibody is produced at high levels by the EE hybridoma. Some have reported that 10 L preps routinely yield 3–5 g of purified antibody. The EE tag has the additional advantage of containinga strong tyrosine phosphorylation substrate for protein kinases such as src. Such a tag may be a useful assay detection label for high throughput protein interaction assays. Such a tag may be directly labeled with radioactive phosphate or detected with an anti-phosphotyrosine antibody.

In a fourth aspect, the present invention features a method for determining the function of foreign genetic material comprising the steps of: (a) providing a baculovirus transfer vector comprising one or more selectable marker genes, a promoter such as a polyhedrin promoter of a polyhedrin structural gene or a fragment thereof, a transcription termination sequence such as a transcription termination sequence of a polyhedrin structural gene or fragment thereof, a cloning site operable to accept foreign genetic material, optionally a tag and optionally one or more restriction sites, (b) ligating foreign genetic material into the baculovirus transfer vector at the cloning site such that the foreign genetic material is under the control of the promoter, (c) transfecting the baculovirus comprising the foreign genetic material into a host cell, and (d) observing the biological results produced thereby. In preferred embodiments, the present invention is adapted to automation and thereby is useful for high throughput analysis.

Those of skill in the art will readily understand that there are many methods to determine the function of foreign genetic material once expression in a host, such as an insect cell is attained. In one embodiment the function of a nucleic acid may be determined by complementation analysis. That is, the function of the nucleic acid of interest may be determined by observing the endogenous gene or genes whose function is replaced or augmented by introducing the nucleic acid of interest. In a second embodiment, the function of a nucleic acid may be determined by analyzing the biochemical alterations in the accumulation of substrates or products from enzymatic reactions according to any one of the means known by those skilled in the art. In a third embodiment, the function of a nucleic acid may be determined by observing phenotypic changes in the host by methods including morphological, macroscopic or microscopic analysis. In a fourth embodiment, the function of a nucleic acid may be determined by observing the change in biochemical pathways which may be modified in the host as a result of the local and/or systemic expression of the foreign genetic material. In a fifth embodiment, the function of a nucleic acid may be determined utilizing techniques known by those skilled in the art to observe inhibition of gene expression in the cytoplasm of host cells as a result of expression of the foreign genetic material.

A particularly useful way to determine gene function is by observing the phenotype in an organism when a particular foreign genetic material has been expressed therein. Useful phenotypic traits in organisms which may be observed microscopically, macroscopically or by other methods include, but are not limited to, improved tolerance to insecticides, improved tolerance to extremes of heat or cold, drought, salinity or osmotic stress; improved resistance to diseases (fungal, bacterial or viral), production of enzymes or secondary metabolites; and the like. Other examples include the production of important proteins or other products for example antibodies, hormones, pharmaceuticals, antibiotics and the like. The phenotypic trait may also be a secondary metabolite whose production is desired.

One strategy that has been proposed to assist in such efforts is to create a database of expressed sequence tags (ESTs) that can be used to identify expressed genes. Accumulation and analysis of expressed sequence tags (ESTs) have become an important component of genome research. EST data may be used to identify gene products and thereby accelerate gene cloning. Various sequence databases have been established in an effort to store and relate the tremendous amount of sequence information being generated by the ongoing sequencing efforts. It is specifically contemplated that the present method may be used to expedite efforts to isolate functional genes and determine the biological function thereof.

In a fifth aspect, the present invention features genes and fragments thereof, nucleotide sequences, and gene products obtained by way of the method of the present invention. The present invention features expressing selected foreign genetic material including nucleotide sequences in a host cell. Those of skill in the art will readily appreciate that the gene products of such foreign genetic material may be isolated using techniques known to those skilled in the art. Such gene products may exhibit biological activity such as pharmaceuticals and other similar fanctions.

The following definitions are provided to further clarify the present invention. No particular definition is intended to be limiting but is rather provided to clarify the meaning of the terms as used herein.

Expressed sequence tags (ESTs): Relatively short single-pass DNA sequences obtained from one or more ends of cDNA clones and RNA derived therefrom. They may be present in either the 5' or the 3' orientation. ESTs have been shown usefuil for identifying particular genes.

Expression: The term as used herein is meant to incorporate one or more of transcription, reverse transcription and translation.

Gene: A discrete nucleic acid sequence responsible for producing one or more cellular products and/or performing one or more intercellular or intracellular functions.

Host: A cell, tissue or organism capable of replicating foreign genetic material such as a nucleic acid and which is capable of being transfected with the same as, for example, by way of a baculovirus or transfer vector fragment thereof. This term is intended to include prokaryotic and eukaryotic cells, organs, tissues or organisms, where appropriate.

Transfer vector: A nucleotide sequence operable to transfer foreign genetic material into a host cell to effect subsequent transcription and/or translation of the foreign genetic material. Specifically intended within the scope of this term are baculoviruses and fragments thereof including those fragments which are linearized.

EXAMPLES OF THE PREFERRED
EMBODIMENTS

The following examples further illustrate the present invention. These examples are intended merely to be illustrative of the present invention and are not to be construed as being limiting. The examples are intended specifically to illustrate that foreign genetic material may be expressed by way of recombinant baculovirus expression systems in a host insect cell in an automated fashion to rapidly effect production of proteins and peptides and to subsequently assess the function thereof.

Example 1
Selecting and Re-arraying cDNA into 96-well Format

We will choose a group of genes for which CDNA clones are available. We will re-array the cDNA clones into 96 plate format. Re-arraying robots such as those in use at Lawrence Livermore National Laboratories may be used for this project. We will sequence verify the identity of clones on an as needed basis. Some clones will be seeded into multiple wells to allow for preliminary estimates of reproducibility between wells. We will also initiate the data tracking process such that information regarding clone identifiers, sequence accession numbers, passage number, etc are available for each re-arrayed plate. Clones chosen will also represent a mix of known and unknown clones. For the known clones, we will include both some full and some partial representatives.

Example 2
Amplification of Arrayed cDNAs

We will directly transfect amplified cDNA that has been ligated to linear recombinant baculovirus expression systems (transfer vectors) containing the required recombination and expression elements. This will minimize the number of steps required to automate this process and provide maximum flexibility in handling a diverse collection of cDNA clones.

PCR primers appropriate for each cDNA library vector will be designed and synthesized. The primers will include restriction sites for directed ligation to the transfer vector fragments. cDNA inserts will be amplified using these primers, cut with the appropriate restriction enzymes, ligated to transfer vector fragments, purified if necessary and transfected to insect cells. The supernatant from these transfected cells will be passaged to produce high-titer recombinant virus stock. The possibility of using undigested PCR products for directed single base overhang ligations will also be investigated. It is important to use the highest-fidelity thermostable polymerases available as well as the minimum number of amplification cycles to reduce any sequence infidelities.

In order to assure that each cDNA insert is in proper reading frame with respect to the start codon in the transfer vector, the appropriate transfer vector for each cDNA clone must be selected. This may be done by programmning a robotic pipettor to pick up the correct vector based on an analysis of the known 5' (EST) sequence of the cDNA clone.

Example 3
Construction of Baculovirus Transfer Vectors to Accept and Adapt Amplified cDNA A new series of expression vectors will be constructed to facilitate the cloning of CDNA fragments from the cDNA libraries available. These expression vectors will take advantage of recent developments in insect cell expression. Recombinant baculoviruses can be generated by transfecting insect cells with ligated fragments containing transfer vector elements and cDNA inserts rather than cloned transfer vector plasmids. This greatly simplifies the process of obtaining recombinant baculoviruses by eliminating the plasmid cloning steps. These vectors will include unique restriction enzyme sites such as SfiI and NotI specific for the primers that will be used to amplify the cDNA inserts. The protein products expressed by these vectors will therefore have the EE tag at the N-terminus followed by 2–4 amino acids derived from a linker sequence.

A baculovirus puromycin resistance (pac) gene has been identified that confers increased viral yield in certain cell lines. (Vara, et al., *Nucleic Acids Res.* 14: 4617–4624 (1986). We will include this gene in our vector design and eliminate it from our host virus strain to ensure that the percentage of recombinant baculovirus in our virus stocks is maintained at close to 100%. More specifically, the puromycin resistance (pac) gene will be inserted upstream from the polyhedrin promoter. This will provide an additional selection for recombinant virus as the vectors will be used with a baculovirus strain that lacks the pac gene. These vectors will be otherwise identical to the pAcoG and pAcOGS vectors from which they will be derived.

These vectors will be cotransfected with DNA from polyBsu2, a baculovirus strain developed at Cetus Corporation (Martha Stampfer and Robin Clark, unpublished). It contains three Bsu36I sites which, when cut, remove the essential ORF-1629 gene from the baculovirus genome. Thus the strain is very similar to a strain previously described. (Kitts et al., *Biotechniques* 14:810–817 (1993)) The viability of Bsu361 digested polyBsu2 DNA can only be restored by recombination with transfer vector DNA containing ORF-1629. The strain will be modified using standard recombination methods to inactivate the puromycin resistance (sac) gene.

Example 4
Preparing Recombinant Baculovirus by Direct Transfection of Ligated DNA A number of aspects of insect cell culture may be optimized in order to develop particularly robust formats. For example, a Sf9 host cell inoculation may be optimized with regards to inoculation density for cells in 96 well plates.

In some experiments designed to simulate a high throughput and/or automated protocol, we used a Sf9 inoculum derived from a large culture, grew the inoculum in a serum free insect medium, and cultured the cells in 96 well tissue culture plates at varying densities. We achieved inoculum densities resulting in reproducible exponential growth over 24 hours. Thus, such cultures will allow the generation of cultures in optimal condition for both infection with recombinant baculoviruses and cotransfection with donor transfer vectors and acceptor baculovirus DNA.

Example 5

We will optimize methods for producing proteins from recombinant baculovirus expression systems. However, it is presently contemplated that those methods presently available and described in the literature are acceptable. Miniaturization and automation of required operations including cell culture, infections, harvesting infected cells, preparing lysates, affinity chromatography and storage of purified proteins may be optimized according to known procedures without undue experimentation.

Example 6
Affinity Purification of Recombinant Proteins using the Glu-Glu Tag

Purifying the desired product from baculovirus infected cells may be performed according to any one of many protocols. Many expression vectors have been developed enabling synthesis of the antigen of interest as a fusion with a polypeptide facilitating purification. For instance, protein A fusion proteins may be affinity purified on IgG, polyarginine fusion proteins may be purified by cation exchange, polyhistidine fusions may be purified by virtue of their chelation of zinc ions, β-galactosidase fusions, and other fusions to specifically immunogenic partners may be purified by immunoaffinity and β-galactosidase, maltose binding protein and glutathione-S-transferase (GST) fusion proteins may be purified by substrate affinity.

An epitope tag recognized by the EE or Glu-Glu antipeptide antibody may also be used. Grussenmeyer et al, *Proc. Natl. Acad. Sci.* 82: 7952–7954 (1985). This antibody was raised against a peptide that comprises the major tyrosine phosphorylation site of polyoma middle T antigen. Talmage et al., *Cell* 59:55–65 (1989) The use of this tag for protein purification was developed at Cetus Corporation (Rubinfeld et al., *Cell* 65:1033–1042 (1991)) and has been the primary tag used for this purpose at Chiron Corporation. The epitope for this tag has been fully characterized and optimized by Mimotope peptide scan analysis (Mario Geysen, John Wang and Robin Clark, unpublished data). The antibody has moderate affinity for the tag (Kd approximately $2 \times 10^{-7}$) which allows rapid elution of tagged proteins by free peptide under nondenaturing conditions while retaining efficient binding of proteins in crude lysates. While usually placed at the N-terminus, the tag is recognized when placed at the C-terminus or internal portions of the protein. The antibody is also useful for immunoprecipitates, immunofluorescence and western blots. Garcia et al., *Mol. Cell Biol.* 13:6615–6620(1993) Supply of this antibody is not aproblem as it is produced by the BE hybridoma at high levels. 10 L preparations have routinely yielded 3–5 g of purified antibody. The EE tag has the additional advantage of containing a very strong tyrosine phosphorylation substrate for protein kinases such as src. Garcia et al., *J. Biol. Chem.* 268:25146–25151 (1993) This feature will be useful as an assay detection label for high throughput protein interaction assays. It may be directly labeled with radioactive phosphate or detected with an anti-phosphotyrosine antibody.

The use of the EE tag has been facilitated by a series of baculovirus expression vectors, designated as pAcOG1, 2, and 3, in which the original polylinker of pAcC13 was replaced with a synthetic polylinker encoding an initiating methionine, the Glu-Glu epitope tag and multiple single restriction enzyme sites in all three frames. Munemitsu et al., *Mol. Cell. BioL* 10:597–5982 (1990). These vectors allow one-step construction of baculovirus expression vectors in which insert coding sequence (with native stop codon) is fused to an N-terminal EE tag in frame. Another set of vectors, pAcO GlS, 2S, and 3S, also contain a series of tandem stops in all three frames for partial constructs which do not bring along their own stop codon. The order of the sites was influenced by the most commonly found restriction enzymes utilized for the creation of cDNA libraries. The vector itself was optimized for expression by including unique sequences upstream and downstream of the initiating methionine which were experimentally determined to enhance expression in Sf9 cells. These vectors have been used to produce many EE-tagged proteins.

Figure 4:
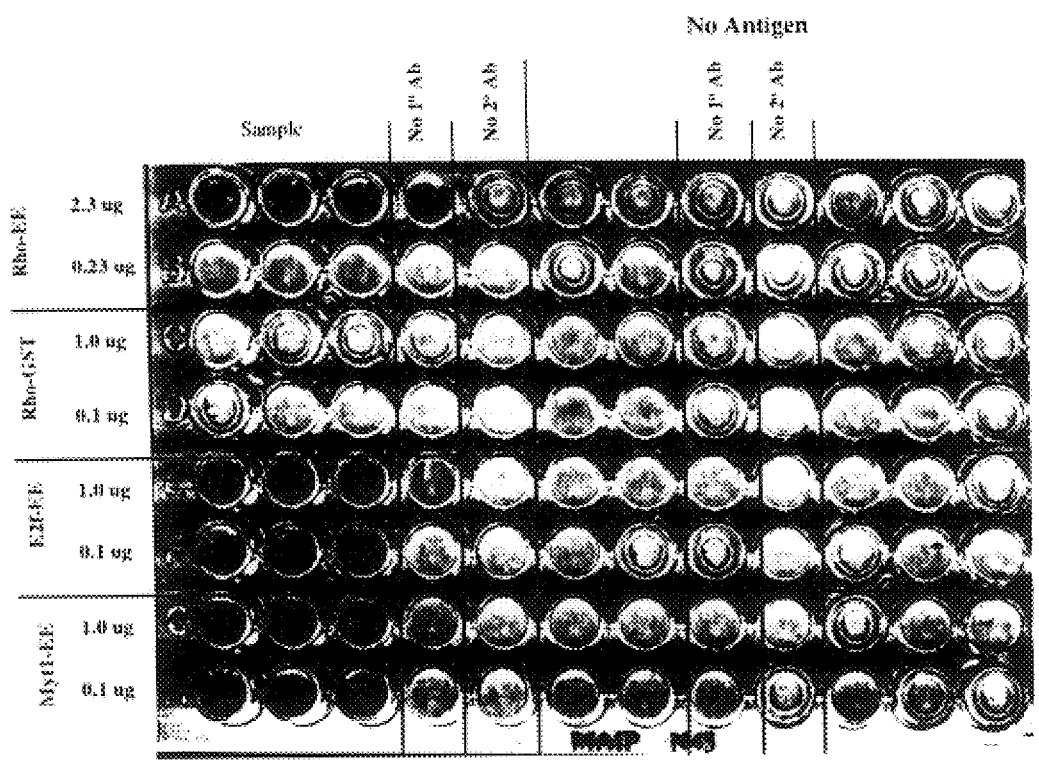
Figure 5:
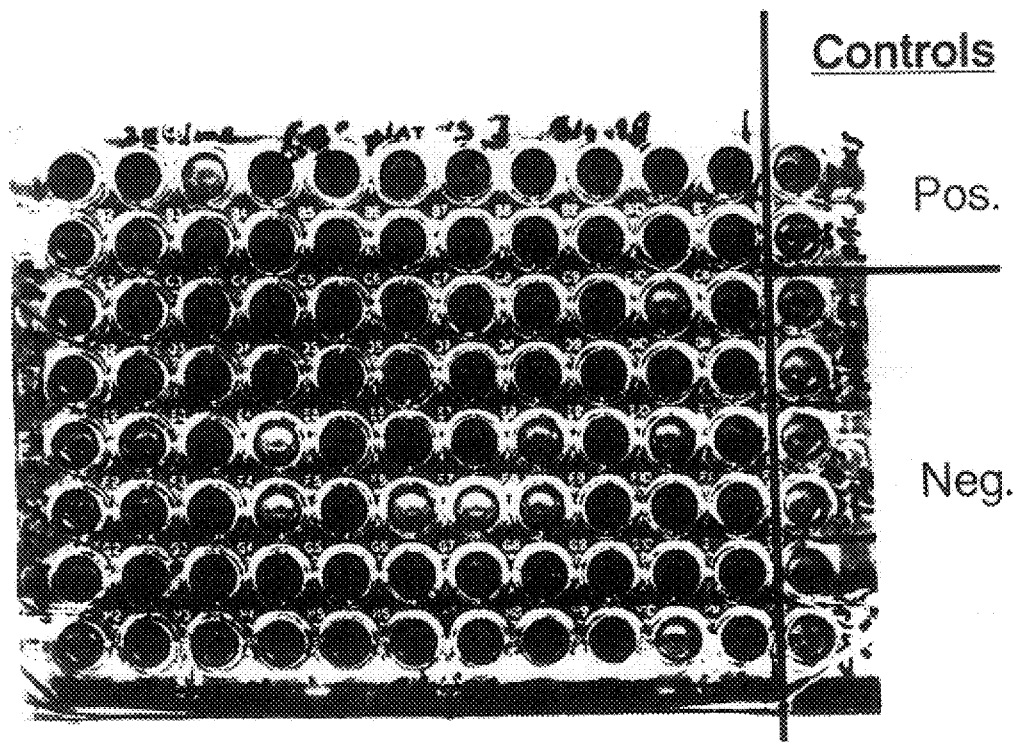
FIG. 5 shows that the scanned image of a 96-well plate shows that recombinant baculoviruses can be efficiently produced without any cloning steps using the invention methods.

To demonstrate that Glu-tagged proteins may be conveniently immunoassayed in a 96-well format amenable to high throughput automation, we performed the following experiment. Millipore MAIP N45 high protein binding plates containing Immobilon-P filtration membranes were treated with either Glu-tagged or GST-tagged proteins and assayed for binding using a monoclonal anti-Glu-Glu antibody and an alkaline phosphatase conjugated goat antimouse IgG secondary antibody. Alkaline phosphatase was detected using SigmaFast BCIP/NBT tablets. As shown in FIG. 4, purified Rho-EE, E2F-EE and Myt1-EE were detected at concentrations ranging from 0.1 to 2.0 µg/well. These results demonstrate that the Glu-tag is a convenient and specific immunoassay target for quantifying recombinant proteins in a 96-well format. Furthermore, this technique is easily adapted to a limiting dilution assay for screening of recombinant baculovirus, and could also be adapted for in situ detection of recombinant proteins in a 96-well tissue culture wherein they have been produced.

Example 7

These data demonstrate that it is feasible to perform an enzyme assay on a baculovirus-expressed recombinant protein in the same 96-well format in which the Sf9 cells were seeded and infected with virus. We used a virus expressing an enzyme which can easily be assayed calorimetrically (e.g. Gus). However, the same principles may be extended to proteins with other functions.

Enzymatic detection of recombinant proteins in a 96-well plate format was tested using a recombinant baculovirus expressing β-glucuronidase (Gus). Sf9 cells grown in insect serum free medium were grown to mid-log phase and used to seed 96-well flat bottom polystyrene tissue culture plates at a density of 40,000 cells/100 µl/well. rgus virus was serially diluted in 10-fold increments. After addition of virus dilutions, the plate was incubated for several days, and then X-glucuronide stock was added to each well. X-glucuronide is a histochemical substrate for β-glucuronidase, yielding a blue substrate upon hydrolysis.

Figure 3:
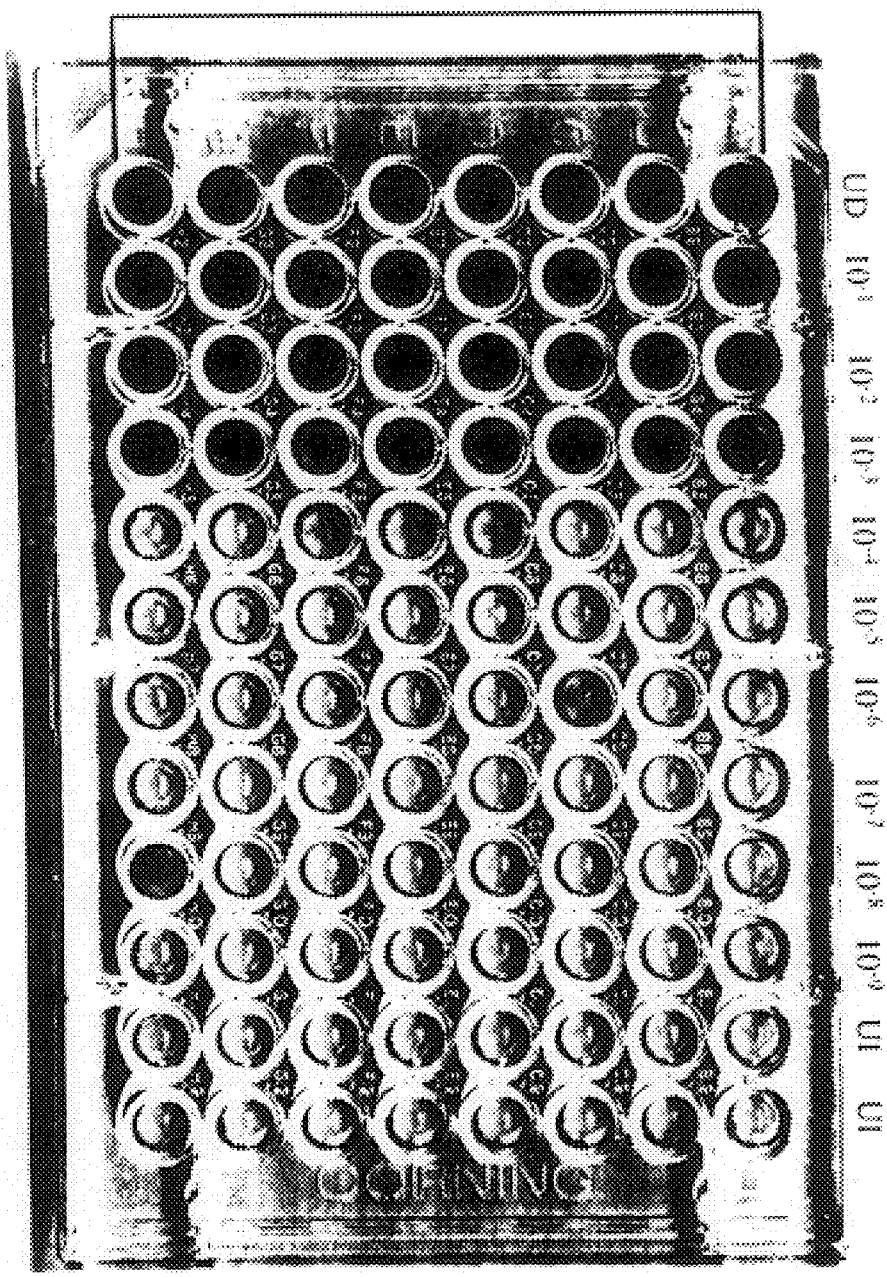
FIG. 3 demonstrates enzymatic detection of recombinant proteins in a 96-well plate format using a recombinant baculovirus expressing β-glucuronidase (Gus). Sf9 cells grown in insect serum free medium were grown to mid-log phase and used to seed 96-well flat bottom polystyrene tissue culture plates at a density of 40,000 cells/100 µl/well.

Blue color development was visible in many wells within minutes after addition of the substrate, and color development continued to occur in high dilution wells over 24 hours as rGus production increased in infections resulting from low MOI's. Color development was visible both in the supernatant of infected wells as well as within individual cells when examined microscopically. These results as demonstrated in FIG. 3 indicate that enzymatic activity is easily detectable in baculovirus infected cultures where low cell numbers are infected at low MOI. Thus, this and related enzymatic assays in situ following baculovirus infection may be adaptable to high throughput automation.

Example 8

Figure 2:
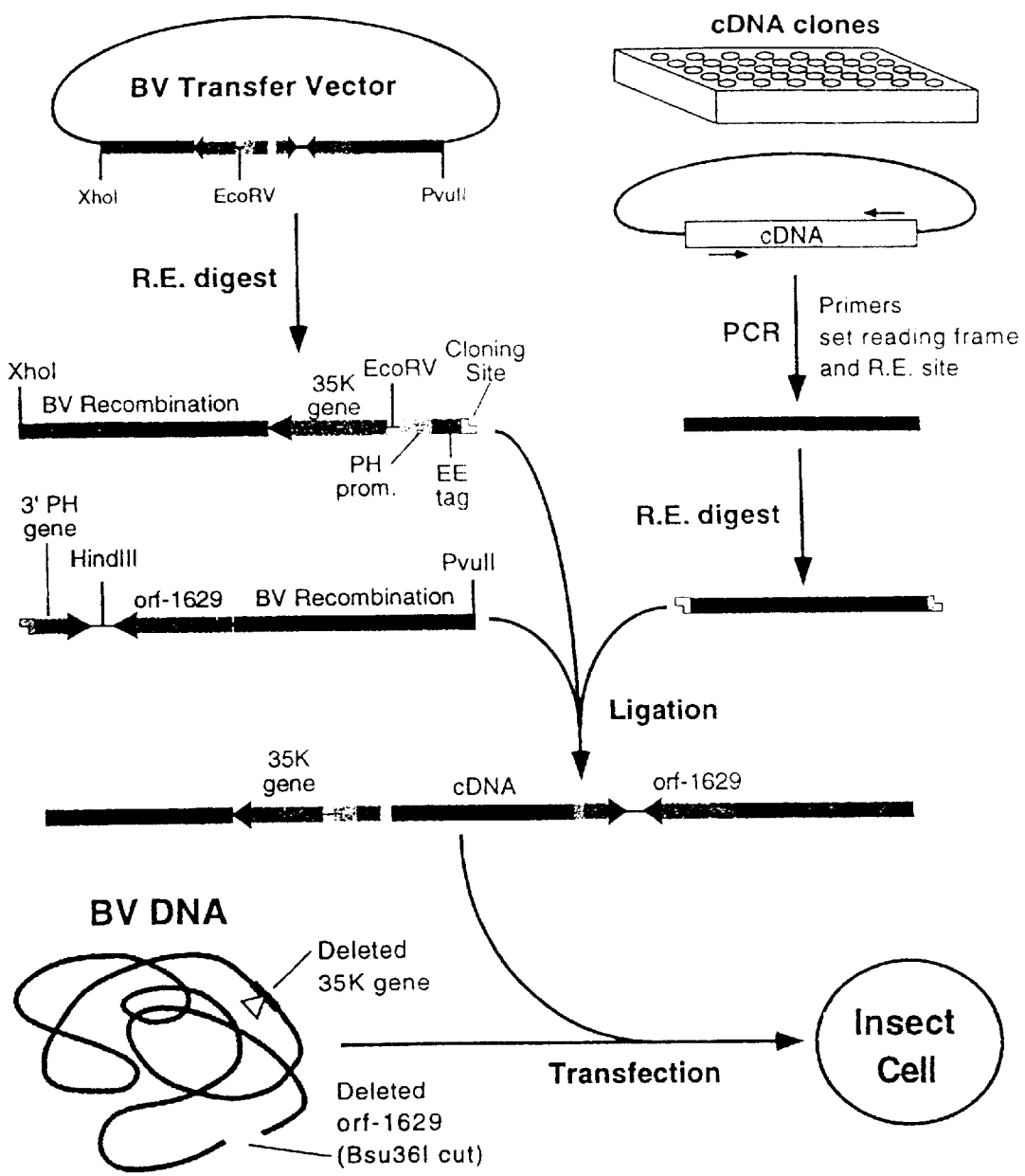
FIG. 2 demonstrates the applicability of the present invention to expressing genetic material such as EST cDNA clones. A baculovirus comprising a puromycin resistance (pac) gene, a polyhedrin promoter, an EE tag, and a cloning site under the control of the polyhedrin promoter may be ligated to foreign genetic material such as EST cDNA clones such that the foreign genetic material is expressed at high levels. The baculovirus expression system containing the foreign genetic material may then be transfected into host cells such as insect cells to effect expression of the product of the genetic material. EST cDNA clones may be amplified according to PCR procedures well known in the art and suitably prepared for cloning into the cloning site of interest. Such a procedure results in high transcription and high translation rates of the foreign genetic material thereby allowing for high level protein production and enabling rapid analysis of gene functions.

This example demonstrates some principles of the present invention wherein a recombinant baculovirus is produced from a cDNA clone in a miniaturized (96-well) format with no cloning steps. The principle elements of this procedure are diagrammed in FIG. 2, discussed supra.

Step 1: Bacterial cultures containing a cDNA clone plasmid are arrayed in a 96-well plate. The plasmid is a Bluescript cDNA library vector which contains the GUS gene, which is commonly used as an expression marker.

Step 2: The GUS gene insert is amplified by PCR procedures using primers that hybridize to a plasmid vector sequence on either side of the cDNA insertion site. These primers also contain restriction sites (NotI for the 5' primer and SfiI for the 3' primer) in the 5' ends of the primers. The portion of the primer containing the restriction sites does not hybridize to the plasmid vector sequence, but is incorporated into the PCR product.

Step 3: The PCR products from step 2 are digested with NotI and SfiI restriction endonucleases to generate the appropriate sticky ends on the products.

Step 4: The restriction fragments generated in step 3 are purified by chromatography on an Arrayit 96-well DNA purification apparatus.

Step 5: Baculovirus transfer vector arms are generated by digesting pAcOP2 with NotI, SfiI, Pvu2 and XhoI. The pAcOP2 plasmid contains the EE epitope tag followed by a cloning site containing NotI and SfiI restriction sites. The EE tag includes a start codon and is positioned to be transcribed by a polyhedrin promoter. pAcOP2 also contains the orf-629 and p35 selectable markers and thus is an example of the baculovirus transfer vector depicted in FIG. 2, described supra. The DNA from this restriction digest is purified by chromatography on a Qiagen column.

Step 6: The restriction fragments from steps 4 and 5 are mixed and ligated together with DNA ligase.

Step 7: Baculovirus DNA containing a Bsu36I restriction endonuclease site in the orf-1629 region (poly Bsu2) is digested with Bsu36I to generate linearized fragments that lack a complete orf-1629 gene.

Step 8: The ligation products from step 6 are co-transfected into insect (Sf9) cells (seeded in a 96-well plate) with baculovirus DNA from step 7 using standard insect cell transfection protocols such as the Invitrogen lipofection method.

Step 9: The transfected Sf9 cultures from step 8 are incubated 5 days. The resulting baculovirus stock is passaged 2 times on Sf9 cells.

Step 10: The passaged virus stock from step 9 is diluted 10-fold into medium containing 150 ug/ml X-gluc and used to infect Sf9 cells in a 96-well plate. Eight of the 96 wells are used for experimental controls.

Step 11: Two days after infection the plate from step 10 is scored for the presence of a blue color in the wells, which indicates the expression of the GUS gene. The percentage of blue wells relative to the total number of wells indicates the efficiency and degree of success of the process.

Example 9

This Example Demonstrates a Method of using the Present Invention.

Step 1: The gene of interest is -amplified from selected and uniquely arrayed cDNA clones by PCR, using primers appropriate for each cDNA library. These primers will include sites for directed ligation to transfer vector arm fragments, also known as arm fragments. The arm fragments contain selectable marker genes such as the puromycin resistance (pac) gene, an orf 1629 gene, recombinagenic sites, and a peptide epitope tag sequence that will fused to the gene of interest. The primers will also set the proper reading frame for fusion to the peptide tag according to known sequence of the CDNA clone.

Step 2: The arm fragments are produced by PCR using primers that add a sequence which facilitates ligation to amplified cDNAs. One of the arm fragments contains the pac gene inserted upstream from the polyhedrin promoter and the sequence that encodes the epitope tag. Translation of the tag sequence is driven by the polyhedrin promoter. The other arm (right arm) contains the orf 1629 gene. These two genes, pac and orf 1629, provide a double selection for recombinant viral production, as the vectors will be used with a baculovirus strain that lacks the pac gene and has been cut with Bsu36I to excise the orf 1629 gene.

Step 3: The PCR-amplified cDNA inserts are digested with T4 polymerase in the presence of one nucleotide triphosphate (Charalampos, et al., *Nucleic Acids Res.* 18:6069–6074 (1990)) This process produces a defined single-stranded overhang on each end of the molecule.

Step 4: These cDNA - containing digestion products are then annealed and ligated to similarly prepared arm fragments, as described in Step 2.

Step 5: A baculovirus strain lacking the pac gene is cut with Bsu36I to excise the orf1629 gene.

Step 6: The ligation product is then purified, if necessary, and transfected into Sf9 insect cells along with viral DNA from Step 6. Homologous recombination between the viral DNA and the ligation product produces a new viral genome containing the gene of interest and both selectable markers.

Step 7: The supernatant from the transfected cells are passaged on Sf9 insect cells in the presence of puromycin to produce high-titer recombinant virus stock. Virus were passaged once on p35pSf9 cells to increase titer and again in the presence of 2 µg/mL puromycin (added one hour post-infection).

We claim:

1. A selection method for producing puromycin resistant recombinant baculovirus expressing a gene of interest comprising:
    a) constructing a piece of linear or circular DNA containing a puromycin resistance gene, a gene of interest, an orf 1629 gene, a peptide epitope tag sequence fused to the gene of interest, one or more additional selectable marker genes, and recombinagenic sites;
    b) recombining said piece of DNA into baculoviral DNA;
    c) co-expressing said puromycin resistance gene and said gene of interest during viral infection; and
    d) selecting said puromycin resistant recombinant baculovirus in the presence of puromycin-containing cell culture media.

2. The method of claim 1, wherein said recombinagenic sites direct the insertion of said piece of linear or circular DNA into the baculoviral DNA by recombination.

3. The method of claim 1 wherein the puromycin resistant gene and orf 1629, provide a double selection for recombinanant vital production.

4. The method of claim 1 wherein said method is specifically designed for automated protein production systems.

5. The method of claim 1 wherein said ligating is performed by automation in an array of multiple wells.

6. A method of constructing said puromycin resistant recombinant baculovirus of claim 1 comprising:
    a) amplifying a gene of interest from selected and uniquely arrayed cDNA clones by polymerase chain reaction (PCR) using primers appropriate for each cDNA library;
    b) digesting said PCR-amplified cDNA inserts with T4 polymerase in the presence of one nucleotide triphosphate to produce defined single-stranded overhang on each end of cDNA inserts;
    c) amplifying by PCR a left and a right arm fragment using primers that facilitate ligation to amplified cDNAs;
    d) annealing and ligating said cDNA-containing digestion products to said arm fragments;
    e) preparing a baculoviral DNA lacking the puromycin resistance gene and an orf 1629 gene, and comprising a promoter such as a polyhedrin promoter of a polyhedrin structural gene or fragment thereof, a transcription termination sequence such as a transcription termination sequence of a polyhedrin structural gene or fragment thereof, and a cloning site operable to accept said ligation product;
    f) purifying and transfecting said ligation product into Sf9 insect cells with said baculoviral DNA; and
    g) collecting and passaging supernatant from said transfected cells on Sf9 insect cells in the presence of puromycin to produce high-titer recombinant stock.

7. The method according to claim 6 wherein said left and right arm fragments contain a puromycin resistance gene, a gene of interest, an orf 1629 gene, a peptide epitope tag sequence fused to the gene of interest, and recombinagenic sites.

8. The method of claim 6 wherein said gene of interest is inserted between two or more selectable markers.

9. The method of claim 6, wherein said recombinagenic sites are located outside of an assembly containing the gene of interest and selectable markers.

10. The method of claim 6, wherein said right arm contains an orf 1629 gene.

11. The method of claim 6, wherein said left arm fragment contains the uromycin resistance gene inserted upstream from a polyhedrin promoter and a sequence encoding said epitope tag.

12. The method of claim 6, wherein translation of the tag sequence is driven by said polyhedrin promoter.

13. The method of claim 6, wherein gene of interest in under the control of the polyhedrin promoter.

14. The method of claim 6, wherein said primers set the proper reading frame for fusion of the gene of interest to the peptide tag according to the known sequence of the cDNA clone.

15. A puromycin resistant recombinant baculovirus comprising a puromycin resistance gene, a gene of interest, an orf 1629 gene, one or more additional selectable marker genes, and recombinagenic sites, a polyhedrin promoter of a polyhedrin structural gene or fragment thereof, a transcription termination sequence such as a transcription termination sequence of a polyhedrin structural gene or fragment thereof, and a cloning site operable to accept foreign genetic material.

* * * * *

UNITED STATES PATENT AND TRADEMARK OFFICE
CERTIFICATE OF CORRECTION

PATENT NO.    : 6,428,960 B1
DATED         : August 6, 2002
INVENTOR(S)   : Robin Clark et al.

It is certified that error appears in the above-identified patent and that said Letters Patent is hereby corrected as shown below:

Column 1,
Line 4, please insert the following caption and paragraph:

-- STATEMENT OF RIGHTS TO INVENTION
  The United States Government has rights in this invention pursuant to a CRADA (TC-TC-1466-97) between Onyx Pharmaceuticals, Inc., and the University of California, which operates the Lawrence Livermore National Laboratory for the United States Department of Energy under Contract No. W-7405-ENG-48. --

Signed and Sealed this

Twenty-second Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,428,960 B1
DATED         : August 6, 2002
INVENTOR(S)   : Robin Clark et al.

It is certified that error appears in the above-identified patent and that said Letters Patent is hereby corrected as shown below:

<u>Title page,</u>
Item [73], please insert a second assignee as follows:
-- The Regents of the University of California, Oakland CA (US) --

Signed and Sealed this

Ninth Day of September, 2003

JAMES E. ROGAN
*Director of the United States Patent and Trademark Office*